United States Patent [19]

Mills et al.

[11] Patent Number: 5,332,737
[45] Date of Patent: Jul. 26, 1994

[54] AMINO-1,3,5-TRIAZINES AND THEIR ANHYDROBASE DERIVATIVES AS AGENTS FOR CARDIOVASCULAR SYSTEM

[75] Inventors: Stuart D. Mills, Macclesfield; Rodney B. Hargreaves, Poynton; Bernard J. McLoughlin, Macclesfield, all of United Kingdom

[73] Assignee: Imperial Chemical Industries PLC, London, England

[21] Appl. No.: 621,677

[22] Filed: Dec. 3, 1990

[30] Foreign Application Priority Data

Dec. 5, 1989 [GB] United Kingdom ............ 8927462.5
Dec. 22, 1989 [GB] United Kingdom ............ 8929020.9

[51] Int. Cl.$^5$ .................. A61K 31/53; C07D 251/40; C07D 251/48
[52] U.S. Cl. ............................. 514/245; 544/194; 544/196; 544/197; 544/200; 544/208; 544/209; 544/211; 544/198
[58] Field of Search ............... 544/194, 196, 197, 198, 544/200, 208, 209, 211, 212; 514/245

[56] References Cited

U.S. PATENT DOCUMENTS

| | | | |
|---|---|---|---|
| 3,729,468 | 4/1973 | Tani et al. | 544/194 |
| 3,759,911 | 9/1973 | Irikura et al. | 544/197 |
| 4,312,988 | 1/1982 | Jacobs, III et al. | 544/197 |

FOREIGN PATENT DOCUMENTS

| | | | |
|---|---|---|---|
| 0090733 | 3/1983 | European Pat. Off. | |
| 0122855 | 4/1984 | European Pat. Off. | |
| 3611427 | 10/1987 | Fed. Rep. of Germany | 544/198 |

OTHER PUBLICATIONS

Csuros et al, Acta Chemica Acad. Sci. Hungaucal 78(4) pp. 409–417, 1973.
English translation of entire article abstrated as Chemical Abstracts, vol. 86, No. 9, Abstr. No. 55393M, 1986.

*Primary Examiner*—Mukund J. Shah
*Assistant Examiner*—Y. N. Gupta
*Attorney, Agent, or Firm*—Cushman, Darby & Cushman

[57] ABSTRACT

This invention concerns novel compounds of the formula I:

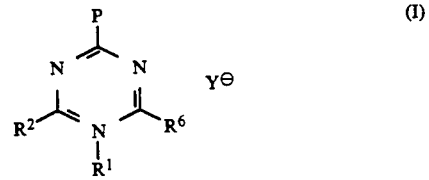

(I)

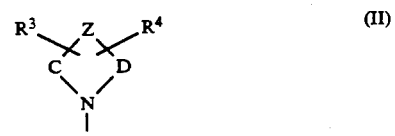

(II)

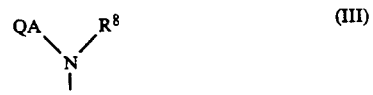

(III)

in which P is a group of formula II or a group of formula III; $R^1$ is alkyl, cycloalkyl, cycloalkylalkyl, phenyl or phenylalkyl; $R^2$ is hydrogen, alkyl, amino or alkylamino; $R^3$ and $R^4$ are independently hydrogen, alkyl, phenyl or benzyl; $R^6$ is alkyl amino or alkylamino; C and D are independently ethylene or trimethylene; Z is a direct bond between C and D, or an oxy, thio, carbonyl, methylene, ethylenedioxymethylene, ethylidene, or isopropylidene link, or Z is a group of the formula $=N.R^5$ in which $R^5$ is alkyl, phenyl or benzyl; R8 is hydrogen, cycloalkylalkyl, alkyl, alkenyl, alkynyl or phenylalkyl; or R8 is a alkylene or alkenylene linked to the nitrogen atom of the group Q.A.N—, either of which linking groups may optionally bear a alkyl, phenyl or phenylalkyl substituent and either of which linking groups thereby completes a ring including two adjacent carbon atoms of ring Q, any carbon atoms in A and the adjacent nitrogen atom of the group —A.N—; A is a direct bond to the the group —N(R8)— or is alkylene; Q is a phenyl or pyridyl moiety; Y is a physiologically acceptable anion; and wherein any one or more of said phenyl, benzene or pyridyl moieties may (Abstract continued on next page.)

optionally be unsubstituted or bear one or more selected substituents.

The invention also includes certain closely related anhydo-base derivatives which, like the compounds of formula I, possess beneficial effects on the cardiovascular system (and in particular beneficial effects modulated via the sino-atrial node). Also included are pharmaceutical compositions containing compounds of formula I (or a related anhydro-base) as active ingrdient, and processes for the manufacture of the various novel compounds.

10 Claims, No Drawings

AMINO-1,3,5-TRIAZINES AND THEIR ANHYDROBASE DERIVATIVES AS AGENTS FOR CARDIOVASCULAR SYSTEM

This invention concerns novel heterocyclic compounds and, more particularly, novel amino 1,3,5-triazine derivatives which possess beneficial effects on the cardiovascular system, pharmaceutical compositions containing such a derivative as active ingredient, and processes for the manufacture of and medical use of the said derivatives.

Although numerous compounds are known to have medically useful effects on the cardiovascular system, hitherto there have not existed satisfactory agents which modulate the action of the sino-atrial node in warm-blooded animals such as man in a beneficial, selective and medically useful manner so that the agents are useful in treating cardiovascular disorders associated with an inappropriately elevated heart rate and yet have minimal effects on other haemodynamic parameters such as blood pressure or cardiac output. It is an object of the invention to provide such an agent.

1,3,5-triazine derivatives have been studied for their herbicidal activity. Such derivatives which are generalky 2,4,6-substitued derivatives are reported in EP 336 494, UK 814947 and UK 1132306. The preparation of selected polyhydro 1,3,5-triazines is reported in Journal. Synthetic Organic Chemistry (Japan), 34, (1976), 417–421.

According to the invention there is provided a compound of the formula I (set out hereinafter, together with the other chemical formulae appearing herein in Roman numerals) wherein:

P is a group of formula II or a group of formula III;

$R^1$ is (1–10C)alkyl, (3–8C)cycloalkyl, (3–8C)cycloalkyl(1–4C)alkyl, phenyl or phenyl(1–4C)alkyl;

$R^2$ is hydrogen, (1–4C)alkyl, amino or (1–4C)alkylamino;

$R^3$ and $R^4$ are independently hydrogen, (1–4C)alkyl, phenyl or benzyl, the latter two optionally bearing one or two substituents selected from (1–4C)alkyl, (1–4C)alkoxy and halogeno; $R^6$ is (1–4C)alkyl, amino or (1–6C)alkylamino; C and D are independently ethylene or trimethylene;

Z is a direct bond between C and D, or an oxy, thio, carbonyl, methylene, ethylenedioxymethylene, ethylidene, or isopropylidene link, or Z is a group of the formula $=N.R^5$ in which $R^5$ is (1–6C)alkyl, phenyl or benzyl, the phenyl moiety of the latter two optionally bearing one or two substituents selected from (1–4C)alkyl, (1–4C)alkoxy and halogeno;

$R^8$ is hydrogen, (3–6C)cycloalkyl(1–4C)alkyl, (1–6C)alkyl, (3–6C)alkenyl (3–6C)alkynyl or phenyl(1–4C)alkyl; or $R^8$ is a (1–4C)alkylene or (2–4C)alkenylene linked to the nitrogen atom of the group Q.A.N—, either of which linking groups may optionally bear a (1–4C)alkyl, phenyl or phenyl(1–4C)alkyl substituent and either of which linking groups thereby completes a ring including two adjacent carbon atoms of ring Q, any carbon atoms in A and the adjacent nitrogen atom of the group —A.N—;

A is a direct bond to the the group —N($R^8$)— or is (1–6C)alkylene;

Q is a phenyl or pyridyl moiety;

Y is a physiologically acceptable anion;

and wherein any one or more of said phenyl, benzene or pyridyl moieties in $R^1$ $R^8$ and Q may optionally be unsubstituted or bear one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy.

It will be understood that when P represents a group of formula III and $R^8$ is hydrogen, or when $R^2$ or $R^6$ is amino or alkylamino, the amino derivatives of the invention may exist in another tautomeric form to that depicted in formula I, or in a mixture of one or more of the possible tautomeric forms. It will also be understood that when P represents a group of formula II and $R^2$ or $R^6$ is amino or alkylamino, the amino derivatives of the invention may exist in another tautomeric form to that depicted in formula I, or in a mixture of one or more of the possible tautomeric forms.

It will also be understood that when one of the substituents in the formula I compounds contains a chiral centre, the compounds of the invention may exist in, and be isolated in, optically active or racemic form. The invention includes any tautomeric, optically active or racemic form of a compound of formula I which possesses the afore-mentioned beneficial pharmacological effects.

The compounds of formula I are quaternary salts and in some cases, for example, when P represents a group of formula III and $R^8$ is hydrogen or $R^2$ or $R^6$ is amino or alkylamino, or when P represents a group of formula II and $R^2$ or $R^6$ is alkyl or alkylamino, may be converted, for example by treatment with a quaternary ammonium hydroxide (and especially one in macroreticular resin form) to the corresponding neutral free bases such as those of the formula IVa or IVb (when P is a group of formula III) or Va or Vb (when P is a group of formula II), respectively, or to a tautomeric form thereof depending on the nature of $R^2 R^4 R^6$. Such neutral free bases of the compounds of formula I, such as those of the formula IVa, IVb, Va or Vb in which $R^7$ is hydrogen or (1–4C)alkyl are provided as a further feature of the invention (provided that when Q is phenyl, A is a direct bond and $R^1$ is phenyl, then $R^2$ and $R^6$ are not both amino) and may readily be reconverted to the quaternary salt form of formula I, for example, by treatment with the appropriate acid of the formula H.Y.

A particular value for $R^1$ when it is alkyl is, for example, (1–6C)alkyl, such as methyl, ethyl, propyl or butyl, of which values methyl and ethyl are generally preferred.

A particular value for $R^1$ when it is cycloalkyl is, for example, cyclopentyl, cyclohexyl or cycloheptyl.

A particular value for $R^2$, $R^3$, $R^4$ or $R^6$ when it is alkyl or for an alkyl substituent when it is present as a part of $R^8$ is, for example, methyl or ethyl.

A particular value for $R^8$ when it is alkyl is, for example, methyl, ethyl, propyl, isopropyl, butyl, iso-butyl or sec-butyl; when it is alkenyl is, for example, allyl, but-2-enyl or 2-methyl-2-propenyl; and when it is alkynyl is, for example, prop-2-ynyl or but-2-ynyl.

A particular value for $R^1$ or $R^8$ when it is cycloalkylalkyl is, for example, cyclopropyl-methyl, cylopentylmethyl, cyclohexylmethyl or 2-(cyclohexyl)ethyl.

A particular value for $R^1$ or $R^8$ when it is phenylalkyl or for a phenylalkyl substituent which is a part of $R^8$ is, for example, benzyl, 1-phenylethyl or 2-phenylethyl.

A particular value for $R^2$ or $R^6$ when it is alkylamino is, for example, methylamino, ethylamino, propylamino or butylamino.

A particular value for $R^8$ when it is alkylene or alkenylene linked to the nitrogen atom of the group Q.A.N— is for example, methylene, ethylidene, ethylene, isopropylidene, trimethylene, tetramethylene, vinylene or 1,3-propenylene; and a particular value for a substituent which may be present on such a linking group is, for example, methyl, ethyl, propyl, butyl, phenyl, benzyl, 1-phenylethyl or 2-phenylethyl (the benzene moiety of any of the last four groups themselves optionally substituted as defined above).

A particular value for A when it is alkylene is, for example, methylene, ethylene, trimethylene or tetramethylene, any of which may optionally bear one or two methyl substituents.

A preferred value for A is, for example, when it is a direct bond, methylene or ethylene.

Particular values for optional substituents which may be present on a phenyl, pyridyl, or benzene moiety in $R^1$, $R^3$, $R^4$, $R^5$, $R^8$ or Q as defined hereinabove include, by way of example: for halogeno, fluoro, chloro and bromo;

for alkyl, methyl and ethyl;
for alkenyl, allyl;
for alkoxy, methoxy and ethoxy;
for alkylamino, methylamino and ethylamino;
for dialkylamino, dimethylamino and diethylamino;
for alkylthio, methylthio and ethylthio;
for alkylsulphinyl, methylsulphinyl and ethylsulphinyl;
for alkylsulphonyl, methylsulphonyl and ethylsulphonyl; and
for alkylenedioxy, methylenedioxy and isopropylidenedioxy.

A particular value for $R^5$ when it is alkyl is, for example, methyl, ethyl, propyl or butyl.

Particular values for the group —C.Z.D— include, for example, tetramethylene, ethyleneoxyethylene [—CH$_2$CH$_2$.O.CH$_2$CH$_2$—], ethyleneoxytrimethylene [—CH$_2$CH$_2$.O.CH$_2$CH$_2$CH$_2$—], ethylenethioethylene [—CH$_2$CH$_2$.S.CH$_2$CH$_2$—], pentamethylene, hexamethylene, ethylenecarbonylethylene [—CH$_2$CH$_2$.CO.CH$_2$CH$_2$—] ethylene(ethylenedioxymethylene)ethylene and groups of the formula —CH$_2$CH$_2$.NR.CH$_2$CH$_2$— and —CH$_2$CH$_2$.NR.CH$_2$CH$_2$CH$_2$— in which R is methyl, ethyl, propyl, butyl or phenyl, the latter optionally bearing a substituent as defined for $R^5$ above. Preferred values for substituents $R^3$ and $R^4$ on any of the above values of —C.Z.D— include, for example, when they are both hydrogen or methyl, or when one is hydrogen and the other is methyl, ethyl, phenyl or benzyl, the latter two optionally substituted as defined above. A further group of preferred values for substituents $R^3$ and $R^4$ on any of the above values of —C.Z.D— include, for example, when they are both hydrogen or methyl, or when one is hydrogen and the other is methyl or phenyl, optionally substituted as defined above.

In general, when Q is a phenyl or benzene moiety it is preferably unsubstituted or else may bear up to three substituents; and when Q is a pyridyl moiety it is preferably unsubstituted or else may bear one or two substituents.

It is generally preferred that $R^2$ is hydrogen or alkyl, and $R^6$ is amino or alkylamino (especially alkylamino). By way of example, a preferred value for Q is phenyl (optionally substituted as indicated herein), and for A is a direct bond.

Specific values for Q include, for example, phenyl, 4-chlorophenyl, 4-methylphenyl, 2-nitrophenyl, 2-methoxyphenyl, 4-methylthiophenyl, 2,5-dinitrophenyl, 3,5-dimethylphenyl, 3,5-dichlorophenyl and pyridyl.

Specific values for the group Q.A.N($R^8$)— when $R^8$ is alkylene or alkenylene include, for example, 1-indolinyl, 1-indolyl, 3-methyl-1-indolyl, 3-methyl-1-indolinyl, 3-ethyl-1-indolyl, 3-ethyl-1-indolinyl, 5-bromo-1-indolyl, 1,2,3,4-tetrahydro-1-quinolyl, 1,2,3,4-tetrahydro-2-isoquinolyl, 5-aza-1-indolinyl. More specific values for the group Q.A.N($R^8$)— when $R^8$ is alkylene or alkenylene include, for example, 3-propyl-1-indolyl and 3-propyl-1-indolinyl. 2-methyl-1-indolyl and 2-methyl-1-indolinyl.

Specific values of particular interest for the group Q.A.N($R^8$)— when $R^8$ is alkylene or alkenylene include, for example, 1-indolinyl, 1-indolyl, 3-methyl-1-indolyl, 3-methyl-1-indolinyl, 3-ethyl-1-indolyl, 3-ethyl-1-indolinyl, 1,2,3,4-tetrahydro-1-quinolyl, 3-propyl-1-indolyl and 3-propyl-1-indolinyl.

Specific values for the group of formula II include, for example, 3-methylpyrrolidino, N-phenylpiperazino, N-(p-chlorophenyl)piperazino, piperidino, 4-phenylpiperidino, 3-methylpiperidino, 3,3-dimethylpiperidino, morpholino, hexamethyleneimino, 3-benzylpiperidino, 4-benzylpiperidino, 2-ethylpiperidino, 3-ethylpiperidino, 3-propylpiperidino, 3-butylpiperidino, 3-phenylpyrollidino and 3,5-dimethylpiperidino (especially cis).

Specific values of special interest for the group of formula II include, for example, 3-methylpyrrolidino, 4-phenyl piperidino, 3-methylpiperidino, 3,3-dimethylpiperidino, 3-benzylpiperidino, 4-benzylpiperidino, 2-ethylpiperidino, 3-ethylpiperidino, 3-propylpiperidino, 3-butylpiperidino, 3-phenylpyrollidino and 3,5-dimethylpiperidino (especially cis).

Specific values for $R^3$ and $R^4$ which are of interest include, for example, hydrogen, methyl, ethyl, propyl, butyl, benzyl and phenyl.

In general, when $R^1$, $R^3$, $R^4$ or $R^5$ contains a phenyl moiety it is preferably unsubstituted or else may bear one or two substituents.

In general, when $R^3$ or $R^4$ includes a benzyl group it is conveniently unsubstituted.

In one embodiment of the present invention there is provided an amino 1,3,5-triazine derivative of the formula I (set our hereinafter, together with the other chemical formulae appearing herein in Roman numerals) wherein P is a group of formula III; $R^1$ is (1–10C)alkyl, (3–8C)cycloalkyl, (3–8C)cycloalkyl-(1–4C)alkyl, phenyl or phenyl(1–4C)alkyl; $R^2$ is hydrogen, (1–4C)alkyl, amino or (1–4C)alkylamino; $R^8$ is hydrogen, (3–6C)cycloalkyl-(1–4C)alkyl, (1–6C)alkyl, (3–6C)alkenyl, (3–6C)alkynyl or phenyl(1–4C)alkyl; or $R^8$ is a (1–4C)alkylene or (2–4C)alkenylene linked to the nitrogen atom of the group Q.A.N—, either of which linking groups may optionally bear a (1–4C)alkyl, phenyl or phenyl(1–4C)alkyl substituent and either of which linking groups thereby completes a ring including two adjacent carbon atoms of ring Q, any carbon atoms in A and the adjacent nitrogen atom of the group —A.N—; $R^6$ is amino, (1–6C)alkylamino or (1–4C)alkyl; A is a direct bond to the the group —N($R^8$)— or is (1–6C)alkylene; Q is a phenyl or pyridyl moiety; Y is a physiologically acceptable anion; and wherein any one or more of said phenyl, benzene or pyridyl moieties may optionally be unsubstituted or bear one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy.

Particular and specific values for the various groups include, for example, the relevant values mentioned hereinabove.

In a further embodiment of the present invention there is provided an amino 1,3,5-triazine derivative of the formula I (set out hereinafter, together with the other chemical formulae appearing herein in Roman numerals) wherein P is a group of formula II; $R^1$ is (1–10C)alkyl, (3–8C)cycloalkyl, (3–8C)cycloalkyl-(1–4C)alkyl, phenyl or phenyl(1–4C)alkyl, the phenyl moiety of the latter two optionally bearing one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy; $R^2$ is hydrogen, (1–4C)alkyl, amino or (1–4C)alkylamino; $R^3$ and $R^4$ are independently hydrogen, (1–4C)alkyl or phenyl, the latter optionally bearing one or two substituents selected from (1–4C)alkyl, (1–4C)alkoxy and halogeno; $R^6$ is (1–4C)alkyl, amino or (1–4C)alkylamino; C and D are independently ethylene or trimethylene; Y is a physiologically acceptable anion; and Z is a direct bond between C and D, or an oxy, thio, carbonyl, methylene, ethylenedioxymethylene, ethylidene, or isopropylidene link, or Z is a group of the formula $=N.R^5$ in which $R^5$ is (1–6C)alkyl, phenyl or benzyl, the phenyl moiety of the latter two optionally bearing one or two substituents selected from (1–4C)alkyl, (1–4C)alkoxy and halogeno.

Particular and specific values for the various groups include, for example, the relevant values mentioned hereinabove.

A group of compounds of the invention which is of particular interest comprises those compounds of the formula XI wherein: Ra is (1–4C)alkyl (especially methyl or ethyl), Rb is (1–4C)alkyl (especially methyl or ethyl); Rc is (1–6C)alkyl, (3–6C)alkenyl, (3–6C)alkynyl or phenyl(1–4C)alkyl; or Rc is (1–4C)alkylene or (2–4C)alkenylene linked to the nitrogen atom of the group Qa.Aa.N—, either of which linking groups may optionally bear a (1–4C)alkyl substituent and either of which linking groups thereby completes a ring including two adjacent carbon atoms of Q and the nitrogen of group —Aa.N—; Rd is (1–4C)alkyl (especially methyl); Qa is phenyl; Aa is a direct bond to the group —NRc—; and Y is a physiologically acceptable anion.

Specific values for Rc and Qa include, for example, the relevant values mentioned hereinabove for $R^8$ and Q.

A preferred value for Ra, Rb or Rd is, for example, methyl.

A further group of compounds of the invention which is of particular interest comprises those compounds of the formula X wherein: Ra is (1–4C)alkyl (especially methyl or ethyl); Rd is (1–4C)alkyl (especially methyl or ethyl); Rb is (1–4C)alkyl (especially methyl); P is a 5-7 membered cyclic aliphatic amino group selected from pyrrolidino, morpholino, piperidino, N-phenylpiperazino, N-(halogenophenyl)-piperazino, N-[(1–4C)alkylphenyl]piperazino, 4-phenyl-piperidino, 4-[(1–4C)alkylphenyl]piperidino, N-[(1–4C)alkoxyphenyl]piperazino, and hexamethyleneimino, any of which groups may optionally bear one or two substituents independently selected from methyl, ethyl, propyl, butyl, phenyl, halogenophenyl and benzyl; and Y is a physiologically acceptable anion.

Specific values for the group P which are of particular interest include, for example, 3-methylpyrrolidino, N-phenylpiperazino, N-(p-chlorophenyl)piperazino, piperidino, 4-phenyl piperidino, 3-methylpiperidino, 3,3-dimethylpiperidino, morpholino, hexamethyleneimino, 3-benzylpiperidino, 4-benzylpiperidino, 2-ethylpiperidino, 3-ethylpiperidino, 3-propylpiperidino, 3-butylpiperidino, 3-phenylpyrrolidino and 3,5-dimethylpiperidino.

Specific values for the group P which are of special interest include, for example, 3-methylpyrrolidino, 4-phenyl piperidino, 3-methylpiperidino, 3,3-dimethylpiperidino, 3-benzylpiperidino, 4-benzylpiperidino, 2-ethylpiperidino, 3-ethylpiperidino, 3-propylpiperidino, 3-butylpiperidino, 3-phenylpyrollidino and 3,5-dimethylpiperidino.

A preferred value for Ra, Rb or Rd is, for example, methyl.

A further group of compounds of the invention which is of particular interest comprises those compounds of the formula X wherein: Ra is (1–4C)alkyl (especially methyl or ethyl); Rd is (1–4C)alkyl (especially methyl or ethyl); Rb is (1–4C)alkyl (especially methyl); P is a 5-7 membered cyclic aliphatic amino group selected from pyrrolidino, morpholino, piperidino, N-phenylpiperazino, N-(halogenophenyl)-piperazino, N-[(1–4C)alkylphenyl]piperazino, N-[(1–4C)alkoxyphenyl]piperazino, and hexamethyleneimino, any of which groups may optionally bear one or two substituents independently selected from methyl, ethyl, phenyl and halogenophenyl; and Y is a physiologically acceptable anion.

Specific values for the group P which are of particular interest include, for example, 3-methylpyrrolidino, N-phenylpiperazino, N-(p-chlorophenyl )piperazino, piperidino, 4-phenylpiperidino, 3-methylpiperidino, 3,3-dimethylpiperidino, morpholino and hexamethyleneimino.

Specific values for the group P which are of special interest include, for example, 3-methylpyrrolidino, 4-phenylpiperidino, 3-methylpiperidino, 3,3-dimethylpiperidino, 3-benzylpiperidino, 4-benzylpiperidino, 2-ethylpiperidino, 3-ethylpiperidino, 3-phenylpyrollidino and 3,5-dimethylpiperidino.

A preferred value for Ra, Rb or Rd is, for example, methyl.

Particular physiologically acceptable counter anions Y include, for example, halide (such as chloride, bromide or iodide), sulphate, phosphate, nitrate, acetate, citrate, fumarate, succinate, trifluoroacetate, methosulphate and p-toluenesulphonate A preferred group of free bases of the invention defined above comprises those compounds of the formula (Xa) in which Ra, Rb, Rd, and P have any of the meanings defined above, and those compounds of formula (XIa) in which Ra, Rb, Rd, Qa, Aa and Rc have any of the meanings defined above.

Compounds of the invention which are of particular interest include the compounds described in Examples 1–3, 5, 6, 8–10, 12–16, 18–21, 27, 33, 37, 38, 40 and 44, of which those descibed in Examples 1, 2, 6, 13, 14, 16, 19, 40 and 44 are of special interest, and those descibed in Examples 1, 6, 16 and 19 are particularly preferred. The above compounds, as described herein (or, in the form of an alternative physiologically acceptable counter anion), are provided as a further feature of the invention.

The compounds of the invention may be obtained by standard procedures of organic chemistry already known to be applicable to the preparation of structurally analogous compounds, for example those procedures described in standard reference works on the chemistry of the 1,3,5-triazines. Such procedures for the manufacture of the novel compounds of formula I are provided as a further feature of the invention and are illustrated by the following preferred processes in which the various generic radicals have any of the meanings defined hereinbefore.

(a) An amino compound of the formula (VI) is reacted with an alkylating agent of the formula R9.Z in which Z is a suitable leaving group and $R^9$ has the same meanings as $R^1$ except phenyl, substituted phenyl (as defined above), (5–10C)alkyl and (3–8C)cycloalkyl.

A preferred value of Z is, for example, halide (especially iodide, bromide or chloride), sulphate, p-toluenesulphate or a group of formula $-OSO_2OR^8$.

The reaction is generally carried out by heating the alkylating agent with the compound of formula (VI) at a temperature of, for example, 40°–120° C. and is conveniently carried out in a suitable solvent or diluent, for example, in an ether such as dioxane, tetrahydrofuran or t-butyl methyl ether. Where the leaving group Z is not the required counterion Y in the required compound of formula (I), it may readily be exchanged by standard techniques mentioned hereinafter.

The starting materials of formula (VI) can be made, for example, by reaction of the corresponding halogeno-1,3,5-triazine of the formula (VII) wherein X is chloro or bromo with the appropriate amine of the formula $Q.A.N(R^8)H$ or of formula (II) at a temperature in the range, for example, 40°–150° C. This particular reaction may be carried out in the presence of a suitable solvent or diluent such as a (1–4C)alkanol or N,N-dimethylformamide, or as a melt of the reagents alone. The amines of the formula $Q.A.N(R^8)H$ and formula (II), and the compounds of formula V are in general known or may be made by conventional techniques well known in the art of organic and heterocyclic chemistry.

Although it will be appreciated that in principle it is possible for alkylation to occur on either of the endocyclic nitrogen atoms, in practice alkylation takes place predominantly on the nitrogen shown bearing $R^1$ in formula (I) and any small amount of the alternative isomer may be removed by well known methods for the purification of organic compounds, for example by chromatographic means or by fractional crystallisation. The position of alkylation can be established by standard techniques, for example by studies of the nuclear Overhauser effect on the proton magnetic resonance of the sample concerned.

(b) Reacting a 1,3,5-triazinium salt of the formula (VIII) wherein X is a suitable leaving group with an amine of the formula $Q.A.N(R^8)H$ or formula (IX).

Suitable values for the leaving group X include, for example halogeno, such as chloro or bromo.

The process will be seen to be analogous to that described above for the production of the starting materials of the formula (VI) and analogous conditions may in general be used. Thus, the process is generally carried out at an elevated temperature in the range, for example, 20°–150° C. and in the presence of a suitable solvent or diluent such as a (1–4C)alkanol or N,N-dimethylformamide.

The 1,3,5-triazinium salts of formula (VIII) may themselves be obtained, for example, by analogy with process (a) above, that is by reaction of a halogeno-1,3,5-triazine of the formula (VII) with the appropriate alkylating agent of the formula R9.Z and in particular an iodide or bromide of the formula $R^9.I$ or $R^9.Br$. Alternatively, they may also be obtained, for example, by reaction of the appropriate 1-substituted 1,3,5-triazin-4-one with a suitable chlorinating agent such as phosphorus oxychloride. The 1-substituted 1,3,5-triasin-4-ones may themselves be obtained by standard procedures of heterocyclic chemistry well known in the art. This procedure is particularly suitable for the production of salts of formula I in which $R^1$ is phenyl or substituted phenyl.

(c) For those compounds of formula I in which $R^6$ is amino or alkylamino, reacting a compound of the formula XII wherein X is a suitable leaving group with an amine selected from ammonia and an amine of the formula $R^7NH_2$.

The group Y represents an appropriate counter ion.

The process is generally carried out at an elevated temperature in the range, for example, 20°–150° C. and in the presence of a suitable solvent or diluent such as a (1–4C)alkanol or N,N-dimethylformamide.

A particularly suitable leaving group X is, for example, halogeno (especially chloro or bromo), dichlorophosphinoyl $[-O.PO.Cl_2]$, or dibromophosphinoyl $[-O.PO.Br_2]$. The latter two groups may conveniently be introduced in situ by the reaction of the corresponding triazinone that is a compound of formula XIII, with phosphorus oxychloride or oxybromide, respectively.

Conveniently, the compound of formula XIII is heated in excess phosphorous oxychloride or oxybromide as appropriate, and the excess reagent is removed, for example by evaporation, before reaction with the amine of formula $R^7NH_2$.

It is preferred that a compound of formula XIII is reacted with phosphorous oxychloride, conveniently with heating, followed by an amine of formula $R^7NH_2$ or ammonia (as appropriate).

The reaction may be accompanied by a "Dimroth rearrangement" {see for example, Ann, 364,183, (1909); 459,39, (1927)} so that the group $R^7$ from the amine $R^7NH_2$ ultimately resides on the ring nitrogen atom which was peviously substituted by $R^1$, and the group $R^1$ is present in the group $R^1NH$ as the $R^6$ substituent. This rearrangement is favoured where the $R^1$ substituent in the compound of formula XII is bulkier than $R^7$. Particularly suitable conditions are when a compound of formula XIII is reacted with phosphorous oxychloride followed by addition of the appropriate amine.

A further suitable leaving group is, for example, alkoxy and in particular ethoxy. Such a group may be introduced by treating the compound of formula XIII with triethyloxonium tetrafluoroborate.

Compounds of formula XIII may be prepared by methods known to those skilled in the art. Scheme 1 illustrates a preparation for compounds of formula XIII.

It will also be appreciated that certain of the various optional substituents in the compounds of the invention may be introduced by standard aromatic substitution reactions or generated by conventional functional group modifications either prior to or immediately following process (a), (b) or (c) above, and as such are included in the process aspect of the invention. Such reactions and modifications include, for example, introduction of nitro or halogeno, reductive alkylation of nitro, oxidation of alkylthio to alkylsulphinyl or alkylsulphonyl and reduction of alkynyl or alkenyl. The reagents and reaction conditions for such procedures are well known in the chemical art.

It will be appreciated that the counter anion $Y^-$ may readily be changed, for example, by reaction of the compound of formula I with a suitable salt such as a silver salt or by ion-exchange chromatography on a column of a basic macroreticular resin in the form of its salt with the desired counter anion, or another conventional method.

When a neutral compound of formula (IVa), (IVb), (Va) or (Vb) is required, it may be obtained, for example, by reaction of the appropriate compound of formula I in which $R^2$ is hydrogen or $R^6$ is amino or alkylamino, with a strong base such as macroreticular resin containing quaternary ammonium hydroxide groups. The process is conveniently carried out by exposing a solution of the compound of formula I in an aqueous solvent such as an aqueous (1-4C)alkanol (for example methanol, ethanol or 2-propanol) to the resin at or near ambient temperature, for example by trickling the solution over a bed or through a column of the resin.

Some of the intermediates of the present invention are novel and are thus provided as further features of the present invention. In particular the present invention provides a compound of formula (VI), wherein P, $R^2$, and $R^6$ may have any of the meanings defined above.

As indicated above, the compounds of the invention possess useful pharmacological properties and modulate the action of the sino-atrial node in warm-blooded animals in a beneficial, selective and medically useful manner so that the agents are useful in treating cardiovascular disorders associated with an inappropriately elevated heart rate and with minimal effects on other haemodynamic parameters such as blood pressure or cardiac output. The beneficial and selective effects of the cardiovascular system may be demonstrated using the following standard laboratory techniques.

a) Bradycardic effect (reduction in beating rate of the spontaneously beating isolated guinea pig right atrium).

This technique involves the dissection of the right atrium from a guinea pig heart, taking care not to damage the sino-atrial node region. The atrium is established in oxygenated (95% $O_2$; 5% $CO_2$) Tyrode's solution [containing 8.0 g NaCl, 0.19 g KCl, 0.025 g $MgCl_2$, 0.05 g $NaH_2PO_4$, 1.0 g $NaHCO_3$, 0.2 g $CaCl_2$ and 2.7 g glucose, per litre of deionised water] between two platinum spikes which are connected via an amplifier to a conventional rate-meter, triggered by the action potentials across the atrium. The preparation is bathed in oxygenated Tyrode's solution at 37 degrees Celsius and allowed to equilibrate for 30 minutes before the addition of a solution of the test compound in a mixture of dimethyl sulphoxide and Cremophor EL, diluted as required with Tyrode's solution. Further solutions of test compound are then added cumulatively at 15 minute intervals or when a steady-state beating rate has been attained. This enables an $IC_{20}$ (i.e. the micromolar concentration required to reduce the beating rate by 20%) to be calculated. Typically, a compound of formula I will have an $IC_{20}$ of 10 micromolar or less.

b) Effect on contractile force of electrically stimulated isolated guinea pig left atrium.

This technique involves the dissection of the left atrium from a guinea pig heart into oxygenated Tyrodes solution. The atrium is then clamped in an polyacrylate plastic holder containing two stainless steel stimulating electrodes. The free end of the atrium (normally the atrial appendage) is attached with silk thread to an isometric force transducer. The atrium is then set under a resting tension of 1 g and is allowed to equilibrate in oxygenated Tyrode's solution for 20 minutes before being stimulated into beating by application of 2.5 Hz, 3 mS pulses at 1.5 times the threshold voltage (normally in the range 3-7 V). A solution ($10^{-5}$ M or less) of the test compound [made up as in (a) above] is then added and the effect on contractile force measured. In this way a comparison of the effect with that of a control solution without any test compound can be obtained. Typically, at a concentration in the range 1-30 micromolar compounds of the formula I show <15% reduction in contractile force.

c) Bradycardic effect in the anaesthetised rat

This technique involves the use of Wistar rats (Alderley Park strain) which are pre-anaesthetised by intravenous injection of alphaxalone/alphadalone (1.5 ml per kg). A polyethylene cannula is inserted into the jugular vein and anaesthesia is maintained by infusion of alphaxalone/alphadalone at a rate of 0.025-0.12 ml per kg per minute. A polyethylene cannula is also inserted into the carotid artery and connected to a pressure transducer filled with physiological saline solution. The arterial blood pressure signal is used to trigger an internally calibrated heart rate meter and the transducer is calibrated with a mercury manometer. The output of the heart rate meter and of the pressure transducer are then recorded simultaneously on a standard chart recorder. After cannulation, the rat preparation is allowed to stabilise for 10 minutes. A solution of a test compound [made up as in (a) above, in a volume of 1 ml per kg] is then administered via the venous cannula in four cumulative doses separated by 5 minute intervals. A group of five rats is used for each test compound. The effects on heart rate and blood pressure may then be determined in comparison with those of a control injection.

Typically, a compound of formula I active using this procedure will require an i.v. dose of 5 mg/kg or less to produce a 30% reduction in heart rate (i.e. the $ED_{30}$ dose).

The beneficial effects of a test compound on the cardiovascular system, such as bradycardic effects without an adverse effect on heart force, blood pressure and or cardiac output, may also be determined in anaesthetised dogs and in dogs in which tachycardia has been induced by exercise. In general, the compounds of the invention show significant and predominantly selective bradycardic effects as evidenced by activity in at least two of the above mentioned test techniques. No overt toxicity is generally observed with the compounds of formula I in the above in vivo test techniques at doses several multiples of those at which significant bradycardic effects are seen.

By way of illustration, the compound described hereinafter in Example 1 had an $IC_{20}$ of about $4.6 \times 10^{-7}$ M in procedure (a) and had an $ED_{30}$ of 0.31 mg/kg i.v. for reduction of heart rate in procedure (c); and the compound described hereinafter in Example 37 had an $IC_{20}$ of about $3 \times 10^{-6}$ M in procedure (a) and had an $ED_{30}$ of 1.1 mg/kg i.v. for reduction of heart rate in procedure (c). Other compounds of formula I, such as those exemplified hereinafter, will typically show activity of the same general order.

As mentioned above the compounds of the present invention are of potential use in treating diseases of the cardiovascular system. Thus there is also provided a compound of the present invention for use in therapy, and the use of a compound of the present invention for the manufacture of a medicament for treating cariovascular disease. The present invention also provides a method of modulating the action of the sino-atrial node in a warm-blooded animal, such as man, requiring such treatment which method comprises administering an effective amount of a compound of the present invention to said animal.

When used in the treatment of diseases of the cardiovascular system, such as myocardial ischaemia affecting warm-blooded animals (and in particular man), it is envisaged that a compound of formula I will be administered orally, intravenously or by some other medically acceptable route (such as by inhalation, insufflation, sub-lingual or transdermal means) so that a dose in the general range, for example, 0.01 mg to 10 mg per kg body weight is received. However, it will be understood that the precise dose administered will necessarily vary according to the nature and severity of the disease and the age and sex of the patient being treated.

In general, the compounds of formula I will usually be administered in the form of a pharmaceutical composition, that is, together with a pharmaceutically acceptable diluent or carrier and such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose form containing, for example, 5–200 mg of the compound of formula I.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example, a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of the new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) conventional abbreviations are used for recrystallisation solvents, for example EtOAc for ethyl acetate, EtOH for ethanol, $Et_2O$ for diethyl ether, IPA for 2-propanol, DMF for N,N-dimethylformamide and IMS for industrial methylated spirits; and (vii) all end-products were characterised by microanalysis, NMR and/or mass spectroscopy.

EXAMPLE 1

A mixture of 4-N-ethylanilino-2-methyl-6-methylamino-1,3,5-triazine (2.0 g, 8.2 mM), methyl iodide (1.54 ml, 24.7 mM) and dioxan (5 ml) was heated at reflux for 16 hours. The mixture was cooled. The solvent was removed in vacuo and the residual solid was triturated with ethyl acetate. The solid was collected by filtration, washed with ethyl acetate, hexane and then recrystallised from a mixture of ethyl acetate and 2-propanol to give 1,2-dimethyl-4-N-ethylanilino-6-methylamino-1,3,5-triazinium iodide as a solid (2.13 g, 67% yield), m.p 161°–171° C.; microanalysis, found: C,43.9; H,5.4; N,18.1%; $C_{14}H_{20}NI$ requires: C,43.65; H,5.23; N,18.18%; NMR: 1.2 (3H,m, $CH_2CH_3$), 2.3–2.35 and 2.6–2.65 (3H, 2s, $CH_3$, rotamers) 2.5–2.6 and 3.0–3.1 (3H, 2d, NH$CH_3$, rotamers) 3.4–3.5 (3H,s, N—$CH_3$), 3.95–4.15 (2H,m, $CH_2$—$CH_3$), 7.25–7.55 (5H, complex, aromatic), 8.45–8.55 and 8.65–8.75 (1H, 2br, NH$CH_3$), rotamers).

[Notes: (i) the rotamer signals coalesced when the NMR spectrum was determined at 100° C. but the $CH_3$ signals were masked by the DMSO and $H_2O$ signals; (ii) the site of quaternisation was confirmed by conventional nuclear Overhauser studies.]

The triazine starting material was prepared as follows: A mixture of 4-chloro-2-methyl-6-methylamino-1,3,5-triazine (0.275 g, 1.7 mM; obtained as described in *J. Pharm. Soc., Japan.,* Vol 95 pp. 512) and N-ethylaniline (0.25 ml, 2.0 mM) was heated at 100° C. for 5 minutes. The product was cooled to ambient temperature, dissolved in a mixture of methylene chloride (15 ml) and 2M hydrochloric acid (10 ml) and stirred for one minute. The methylene chloride layer was separated, washed successively with 2M hydrochloric acid (2×5 ml), water (10 ml), 2M sodium hydroxide (10 ml) and water (10 ml), then dried ($MgSO_4$) and evaporated to dryness. The residual solid obtained was recrystallised from hexane to give 4-N-ethylanilino-2-methyl-6-methylamino-1,3,5-triazine as a solid (0.187 g, 45.3% yield), m.p. 108.5°–109° C.; microanalysis, found: C,64

4; H,6 9; N,28.7%; $C_{13}H_{17}N_5$ requires: C,64.2; H,7.0; N,28.8%; NMR (CDCl$_3$): 1.2 (3H,t, CH$_2$—C$\underline{H}_3$), 2.23 (3H,s, CH$_3$), 2.87 (3H,d NHC$\underline{H}_3$), 2.87 (3H,d, $\overline{NHCH_3}$), 3.02 (2H,q, C$\underline{H}_2$—CH$_3$), 5.05 (1H, br, N$\underline{H}$), 7.20–7.42 (5H, complex, aromatic).

EXAMPLE 2

Using a similar procedure to that described in Example 1, 1,2-dimethyl-4-(3-ethylindol-1-yl)-6-methylamino-1,3,5-triazinium iodide was obtained in 10% yield as a solid, m.p. 275°–276° C. (with decomposition), with microanalysis, found: C,46.9; H,4.8; N,16.7%; $C_{16}H_{20}NI$ requires: C,46.94; H,4.9; N-17.1%; after recrystallisation from ethanol and by reaction of 4-(3-ethylindol-1-yl)-2-methyl-6-methylamino-1,3,5-triazine with methyl iodide.

The starting material was prepared as follows:

(i) A mixture 4-(3-ethylindolin-1-yl)-2-methyl-6-methylamino-1,3,5-triazine (1.5 g, 5.6 mM), 30% w/w palladium on charcoal (0.15 g) and diphenyl ether (10 ml) was heated under reflux in an argon atmosphere for 45 minutes. The mixture was cooled to ambient temperature and methanol (10ml) and methylene chloride (20 ml) were added. The catalyst was removed by filtration through diatomaceous earth. The filtrate was evaporated to low volume by distillation in vacuo and then diluted with hexane (50 ml) to give 4-(3-ethylindol-1-yl)-2-methyl-6-methylamino-1,3,5-triazine as a white solid (1.3 g, 87% yield), m.p. 174°–175° C.; microanalysis, found: C,67.3; H,5.9; N,26.2%; $C_{15}H_{17}N_5$ requires C,67.42; H,6.3; N,26.21%.

(ii) The starting 4-(3-ethylindolin-1-yl)-2-methyl-6-methylamino-1,3,5-triazine was obtained as a solid, m.p. 168°–170°, in a similar manner to that described for the analogous intermediate in Example 1 by reaction of 4-chloro-2-methyl-6-methylamino-1,3,5-triazine with 3-ethylindoline.

EXAMPLES 3–5

The procedure described in Example 1 was repeated using the appropriate substituted amino-1,3,5-triazine of the formula VI (P=formula III, methyl; R$^2$=methyl; R$_6$=methylamino) and an alkylating agent of formula R$_1$.Y. The following compounds of formula I (R$^1$=R$^2$=methyl; R$^6$=methylamino; Y$^-$=odide) were thus obtained:

| Example | [=Q.A.N.(r$^8$)] | Recryt. solvent(s) | m.p. (°C.) | P Yield (%) |
|---|---|---|---|---|
| 3 | 3-ethylindolin-1-yl | dioxan | 234* | 54 |
| 4 | 3-methylindolin-1-yl | IPA/MeOH/EtOAc | 257–258 | 49 |
| 5 | 3-methylindol-1-yl | ethanol | >260 | 4 |

*melting with decomposition

The necessary starting materials of formula VI for Examples 4 and 5 were obtained in analogous manner to those for Examples 3 and 2, respectively, described in connection with Example 2 starting from 4-chloro-2-methyl-6-methylamino-1,3,5-triazine and 3-methylindoline and had the following properties:

2-methyl-6-methylamino-4-(3-methylindolin-1-yl)-1,3,5-triazine, m.p. 149°–151° C.;

2-methyl-6-methylamino-4-(3-methylindol-1-yl)-1,3,5-triazine, m.p. 209°–210° C.

EXAMPLE 6

A column of macroreticular quaternary ammonium anion exchange resin ('Amberlite' IRA400 chloride form: 'Amberlite' is a trade mark of Rohm Haas and Co.) was converted to the quaternary ammonium hydroxide form by eluting the resin with sodium hydroxide (1M solution) until the eluate was free of chloride ions, then washing with deionised water until the eluate was pH=7 and then with 20% v/v ethanol/water (500 ml). A mixture of 1,2-dimethyl-4-N-ethylanilino-6-methylamino-1,3,5-triazinium iodide (0.5 g) and 20% v/v ethanol/water (50 ml) was then loaded onto the column (approximate resin volume 35 ml). The column was eluted with 20% v/v ethanol/water (150 ml). The eluate was evaporated and the resultant solid was triturated with hexane to give 1,2-dimethyl-4-N-ethylanilino-6-methylimino-1,3,5-triazine as a solid (153 mg, 46% yield), m.p. 86°–87° C.; microanalysis, found: C,65.2; H,7.7; N,27.0%, $C_{14}H_{19}N_5$ requires: C,65.34; H,7.44; N,27.21%; NMR: 1.1 (3H, t, CH$_2$C$\underline{H}_3$), 2.2 (3H, s, CH$_3$), 2.8 (3H,s, =N.C$\underline{H}_3$), 3.8 (3H,s, $\overline{N—CH_3}$), 3.9 (2H,q, —C$\underline{H}_2$—CH$_3$), $\overline{7.20}$–7.4 (5H, complex, aromatic).

EXAMPLES 7–19

Using a similar procedure to that described in Example 1, the following compounds of formula I (R$^1$=methyl) were obtained by reaction of the appropriate compound of formula VI with methyl iodide:

| EXAMPLE | R$^2$ | R$^6$ | P [=Q.A.N(R$^8$)] | RECRYST. SOLVENT(S) | M.P. (°C.) | YIELD (%) |
|---|---|---|---|---|---|---|
| 7 | Me | methylamino | anilino | MeOH/Et$_2$O | 269–270 | 21 |
| 8 | Me | methylamino | N-methyl-anilino | MeOH/Et$_2$O | 230–231 | 56 |
| 9 | Me | methylamino | N-propyl-anilino | EtOH/Et$_2$O | 153–153.5 | 54 |
| 10 | Me | methylamino | N-isopropyl-anilino | EtOH/Et$_2$O | 183.5–184 | 69 |
| 11 | Et | methylamino | N-ethyl-anilino | EtOAc | 147–148 | 30 |
| 12 | Me | amino | N-ethyl-anilino | EtOAc/IPA | 229–230 | 59 |
| 13 | Me | methylamino | N-allyl-anilino | EtOH/Et$_2$O | 164–165 | 57 |
| 14 | Me | methylamino | N-2-butynyl-anilino | EtOH/Et$_2$O | 224.5–225 | 62 |
| 15 | Me | methylamino | N-sec-butyl-anilino | EtOH/Et$_2$O | 148–149 | 72 |

-continued

| EXAMPLE | R² | R⁶ | P [=Q.A.N(R⁸)] | RECRYST. SOLVENT(S) | M.P. (°C.) | YIELD (%) |
|---|---|---|---|---|---|---|
| 16 | Me | methylamino | N-cyclopropylmethyl-anilino | MeOH/EtOAc | 169.5–170.5 | 60 |
| 17 | Me | methylamino | N-isobutyl-anilino | EtOAc | 168–169 | 66 |
| 18 | Me | ethylamino | N-allyl-anilino | EtOAc | 158.5–159.5 | 48 |
| 19 | Me | ethylamino | N-ethyl-anilino | * | 153–154 | 48 |

(* purified by column chromatography on silica, eluting with $CH_2Cl_2$).

The necessary starting materials of formula VI (P=Q.A.N(R⁸)— for Examples 7–19 were obtained as solids in an analogous manner to that for Example 1 by reaction of the appropriate 4-chloro-1,3,5-triazine of formula VII (X=chloro) with the appropriate amine of the formula Q.A.N(R⁸)H and had the following properties:

| No. | R² | R⁶ | Q.A.N(R⁸)- | Recryst. solvent(s) | m.p (°C.) | Yield (%) |
|---|---|---|---|---|---|---|
| 1 | Me | methylamino | anilino | MeOH | 156–156.5 | 88 |
| 2 | Me | methylamino | N-methyl-anilino | MeOH | 119–120 | 60 |
| 3 | Me | methylamino | N-propyl-anilino | MeOH | 135–136 | 21 |
| 4 | Me | methylamino | N-iso-propyl-anilino | EtOH/Hexane | 142 | 28 |
| 5 | Et | methylamino | N-ethyl-anilino | Hexane | 79 | 78 |
| 6 | Me | amino | N-ethyl-anilino | EtOAc/Hexane | 145–146 | 9+ |
| 7 | Me | methylamino | N-allyl-anilino | EtOH | 119–119.5 | 18 |
| 8 | Me | methylamino | N-2-butynyl anilino | EtOH | 128.5–129.5 | 47 |
| 9 | Me | methylamino | N-sec-butyl-anilino | MeOH/$H_2O$ | 114–115 | 27 |
| 10 | Me | methylamino | N-cyclopropyl-methyl-anilino | EtOAc | 131.5–132.5 | 74 |
| 11 | Me | methylamino | N-isobutyl-anilino | Hexane | 133.5–134.5 | 79 |
| 12 | Me | ethylamino | N-allyl-anilino | MeOH/$H_2O$ | 72.5–73 | 33 |
| 13 | Me | ethylamino | N-ethyl-anilino | Hexane | 156–157 | 73* |

Notes:
(1) * after purification by column chromatography
(2) 4-chloro-2-ethyl-6-methylamino-1,3,5-triazine, 6-amino-4-chloro-2-methyl-1,3,5-triazine and 4-chloro-6-ethylamino-2-methyl-1,3,5-triazine for starting materials above were obtained as described by T. Tsujikawa et alia in J. Pharm Soc (Japan), 1975, 95, 512.

EXAMPLE 20

Using a similar procedure to that described in Example 1, 4-N-ethylanilino-2-methylamino-1,3,5-triazine was reacted with methyl iodide to afford 4-N-ethylanilino-1-methyl-2-methylamino-1,3,5-triazinium iodide (R¹=methyl, R²=H, R⁶=methylamino, P=QAN(R⁸)=N-ethylanilino; in formula I) in 44% yield as a solid, mp 226°–227° C. (after recrystallisation from isopropyl alcohol).

The starting material was prepared as follows:

(i) Triethylamine (0.16 ml, 1.12 mM) and then a 33% w/v solution of methylamine (0.13 ml, 1.12 mM) in IMS was added at 0° C. to a stirred mixture of 2,4-dichloro-6-N-ethyl-anilino-1,3,5-triazine (obtained as described by PIRKL, J and FISAR, C in Czechoslavakian Patent 171995, 15 March 1978) (0.3 g, 1.12 mM) in methylene chloride (20 ml). The mixture was stirred at 0° C. for 1.5 hours. The mixture was then washed with water (3×20 ml), dried ($MgSO_4$) and evaporated to dryness. There was thus obtained 2-chloro-4-N-ethylanilino-6-methylamino-1,3,5-triazine (0.19 g, 65% yield), m.p. 149°–151° C.

(ii) A mixture of 2-chloro-4-N-ethylanilino-6-methylamino-1,3,5-triazine (1.0 g, 3.8 mM), ammonium formate (1.2 g, 19 mM), 10% w/w palladium on charcoal (0.2 g) and methanol (30 ml) was stirred at 50° C. for 3 hours. The mixture was then evaporated to dryness. The residual solid was dissolved in water (20 ml) and extracted with methylene chloride (3×20 ml). The organic extracts were combined, dried ($MgSO_4$) and evaporated to dryness. The residual solid was recrystallised from hexane. There was thus obtained 2-N-ethylanilino-4-methylamino-1,3,5-triazine (0.46 g, 53% yield), mp 117°–118° C.; microanalysis, found: C, 62.7; H, 6.6; N, 30.2%; $C_{12}H_{15}N_5$ requires: C, 62.9; H, 6.6; N, 30.6%.

EXAMPLES 21–33

Using a similar procedure to that described in Example 1 but starting from the appropriate compound of formula VI and methyl iodide, the following compounds of formula I (R¹=methyl, Y⁻=iodide) were obtained:

| Ex. | R² | R⁶ | P [=Q.A.N.(R⁸)—] | Recryst. Solvent(s) | m.p. (°C.) | Yield % |
|---|---|---|---|---|---|---|
| 21 | Me | methylamino | 3-propyl-indolin-1-yl | Dioxan | 243–244 | 66 |
| 22 | Me | methylamino | 3-propyl-indol-1-yl | Dioxan | 250–252 | 1.5 |
| 23 | Me | methylamino | indol-1-yl | MeOH | 292–293 | 15 |
| 24 | Me | methylamino | indolin-1-yl | EtOH/DMF | 284–286 | 30 |
| 25 | Et | methylamino | indol-1-yl | MeOH | 265 | 9 |
| 26 | Et | methylamino | indolin-1-yl | MeOH | 283 | 34 |

-continued

| Ex. | R² | R⁶ | P [=Q.A.N.(R⁸)—] | Recryst. Solvent(s) | m.p. (°C.) | Yield % |
|---|---|---|---|---|---|---|
| 27 | Me | ethylamino | 3-methyl-indolin-1-yl | EtOH | 151–152 | 59 |
| 28 | Me | ethylamino | 3-methyl-indol-1-yl | MeOH/EtOAc | >260 | 15 |
| 29 | Me | methylamino | 2-methyl indolin-1-yl | EtOH/EtOAc | 233–234 | 33 |
| 30 | Me | methylamino | 2-methyl indol-1-yl | MeOH | >250 | 13 |
| 31 | Me | methylamino | 7-methyl-indolin-1-yl | EtOH/EtOAc | 245–246 | 46 |
| 32 | Me | amino | 3-methyl-indolin-1-yl | EtOAc/EtOH | >260 | 52 |

The necessary starting materials of formula VI were obtained as solids in an analogous manner to that described in Example 3 i.e. by reaction of 4-chloro-2-methyl-6-methyl-amino-1,3,5-triazine, 4-chloro-2-ethyl-6-methylamino-1,3,5-triazine, 4-amino-6-chloro-2-methyl-1,3,5-triazine or 4-chloro-6-ethylamino-2-methyl-1,3,5-triazine as appropriate with the appropriate indoline of the formula Q.A.N(R⁸)H followed by dehydrogenation to the corresponding indol-1-yl derivative, and had the following properties:

dichloro-6-indolin-1-yl-1,3,5-triazine (72.4 g, 87% yield), a portion of which was recrystallised from toluene, mp 254°–256° C. NMR: DMSOd₆: 3.15–3.3 (2H, t, CH₂CH₂—N), 4.05–4.3 (2H, complex, CH₂CH₂N—) (rotamers), 7.0–7.4 (3H, complex, aromatic), 8.15–8.4 (1H, complex, aromatic).

(ii) To a mixture of 2,4-dichloro-6-indolin-1-yl-1,3,5-triazine (30 g, 112 mM) and methylene chloride (300 ml) at 0° C. was added a 33% solution of methylamine (30 ml) in IMS. The mixture was allowed to attain ambient

| No. | R² | R⁶ | Q.A.N.(R⁸)— | Recryst. Solvent(s) | m.p. (°C.) | Yield % |
|---|---|---|---|---|---|---|
| 1 | Me | methylamino | 3-propyl-indolin-1-yl | Et₂O (trituration) | 150–152 | 77 |
| 2 | Me | methylamino | 3-propyl indol-1-yl | EtOAc | 117–119 | 54 |
| 3 | Me | methylamino | indol-1-yl | MeOH/H₂O | 246–247 (with decomp) | 7 |
| 4 | Me | methylamino | indolin-1-yl | EtOH | 201–203 | 69 |
| 5 | Et | methylamino | indol-1-yl | EtOAc/Hexane | 139 | 44 |
| 6 | Et | methylamino | indolin-1-yl | EtOAc | 149–151 | 80 |
| 7 | Me | ethylamino | 3-methyl-indolin-1-yl | *(A) | 129 | 68 |
| 8 | Me | ethylamino | 3-methyl-indol-1-yl | Hexane | 250–251 | 78 |
| 9 | Me | methylamino | 2-methyl-indolin-1-yl | *(A) | 165–166 | 73 |
| 10 | Me | methylamino | 2-methyl-indol-1-yl | Hexane | 168–169 | 56 |
| 11 | Me | methylamino | 7-methyl-indolin-1-yl | *(A) | 168–170 | 91 |
| 12 | Me | amino | 3-methyl-indolin-1-yl | *(B) | 142–143 | 14 |

*purified by column chromatography on silica gel using an elutant of (A) - CH₂Cl₂; or (B) - EtOAc/Hexane

EXAMPLE 33

Using a similar process to that described in Example 1, 2-(indol-1-yl)-4-methylamino-1,3,5-triazine was reacted with methyl iodide to afford 4-methylamino-2-(indol-1-yl)-1-methyl-1,3,5-triazinium iodide in 29% yield as a solid, mp 284°–285° C. (after recrystallisation from methanol).

The starting material was prepared by dehydrogenation of 2-(indolin-1-yl)-4-methylamino-1,3,5-triazine, which was obtained as follows:

(i) To a mixture of cyanuric chloride (50 g, 271 mM), acetone (200 ml) and ice (300 g) was added, over ten minutes, a mixture of indoline (32 ml, 286 mM) and 2.5N hydrochloric acid (120 ml). To this stirred mixture was added, over one hour, a solution of sodium secondary phosphate which had been prepared by neutralising 2.5N sodium hydroxide (250 ml) with orthophosphoric acid to PH 7 to 7.5. The mixture was then stirred for one hour, filtered and the resultant solid was washed with water and dried at 80° C. There was thus obtained 2,4- temperature. After two days the mixture was washed with water. The methylene chloride layer was separated, dried (MgSO₄), and the solvent evaporated. The resultant solid was recrystallised from toluene: ethanol (70:30). There was thus obtained 2-chloro-4-indolin-1-yl-6-methylamino-1,3,5-triazine (24 g, 82% yield). m.p 239°–240° C.; NMR: DMSOd₆: 2.75–2.95 (3H, complex, rotamers, NHMe), 3.05–3.2 (2H, t,CH₂—CH₂N—), 4.0–4.2 (2H,q,CH₂CH₂N) (rotamers), 6.9–7.3(3H, complex, aromatic), 7.9–8.1 (1H, broad, aromatic), 8.1–8.4(1H, broad, NH).

(iii) A mixture of 2-chloro-4-indolin-1-yl-6-methylamino-1,3,5-triazine (5.0 g, 19.1 mM), ammonium formate (6.02 g, 95.6 mM), 10% w/w palladium on charcoal (1.0 g) and methanol (100 ml) was heated at 50° C., under argon, for 6 hours. The mixture was cooled, basified, and filtered. The solid collected by filtration was heated at reflux with ethanol, and the mixture refiltered. The filtrates were combined and the solvent evaporated. The residual solid was washed with water and then purified by flash column chromatography (silica, Merck 9385), eluting with ethyl acetate/hexane (1:3). This gave a solid which was recrystallised from ethyl acetate. There was thus obtained 2-(indolin-1-yl)-4-methylamino-1,3,5-triazine (1.7 g, 39% yield); m.p. 185°–187° C.: micro analysis, found: C, 62.8; H, 6.1; N, 30.3%; $C_{12}H_{13}N_5$. 1/4 $H_2O$ requires: C, 62.2; H, 5.8; N, 30.2%.

EXAMPLE 34

The procedure described in Example 1 was repeated using 2-methyl-6-methylamino-4-(1,2,3,4-tetrahydroquinolin-1-yl)-1,3,5-triazine and methyl iodide. There was thus obtained 1,2-dimethyl-6-methylamino-4-(1,2,3,4-tetrahydroquinolin-1-yl)-1,3,5-triazine, in 12% yield, as a solid, mp 184°–186° C. (with decomposition) after recrystallisation from ethylacetate. NMR: $DMSOd_6$: 1.85–2.1 (2H, complex, —$CH_2$—), 2.5–2.6 (3H,s,$CH_3$), 2.75–2.85(2H,t,—$CH_2$—) 2.85–3.0 (3H,s,NH$CH_3$), 3.45–3.6 (3H,s,N$^+$$CH_3$), 4.0–4.15 (2H,t,—$CH_2$—), 7.1–7.3(4H,complex, aromatic), 7.65–7.85(1H,broad,NH).

The starting material, 2-methyl-6-methylamino-4-(1,2,3,4-tetrahydroquinolin-1-yl)-1,3,5-triazine was obtained in analogous manner to that for Example 1, starting from 4-chloro-2-methyl-6-methylamino-1,3,5-triazine and 1,2,3,4-tetrahydroquinoline to give a solid product, mp 159°–160° C. in 52% yield, microanalysis; found:C, 66.2; H, 6.7; N, 27.4%; $C_{14}H_{17}N_5$ requires; C, 65.9; H, 6.7; N, 27.4.

EXAMPLE 35

A solution of triethyloxonium tetra fluoroborate in methylene chloride (2.5 ml of a 1M solution, 2.5 mM) was added to a stirred solution of 1-n-butyl-4-N-ethylanilino-2-methyl-1,3,5-triazin-6-one (0.36 g, 1.26 mM) in dry methylene chloride (5 ml) at 20° C. After 48 hours, the solution was evaporated to dryness and the residue was dissolved in ethanol (15 ml). This solution was cooled to −20° C. with stirring and a solution of methylamine in IMS (5 ml of 33% w:w solution, an excess) was added slowly at a rate such that the temperature of the reaction did not exceed −15° C. The solution was kept at −20° C. for 1 hour after the addition was complete and then evaporated to dryness. The residue, a yellow gum, was crystallised from a mixture of acetone and diethyl ether to give 1-n-butyl-4-N-ethylanilino-2-methyl-6-methylamino-1,3,5-triazinium tetrafluoroborate as a solid (0.075 g., 16% yield), mp 127°–128° C.; microanalysis, found: C, 52.8; H,6.5; N, 18.0%; $C_{17}H_{26}N_5BF_4$ requires: C, 52.7; H, 6.7; N, 18.1%. NMR: 0.9–1.0(3H,t,$CH_3$), 1.15–1.30(3H,m,$CH_3$), 1.55–1.75(2H,m,$CH_2$) 2.36 and 2.55 (3H,m,$CH_3$, rotamers), 2.65 and 3.0 (3H,m,N—$CH_3$, rotamers), 3.8–3.92(2H, t,N$CH_2$), 4.0–4.15(2H,t,N—$CH_2$), 7.2–7.5(5H, complex, aromatic), 8.4–8.7(1H,br.,NH).

The starting material was prepared as follows:

(i) A mixture of S-methylisothiuronium sulphate (4.9 g, 20 mM), sodium carbonate (4.24 g, 40 mM), water (20 ml) and ethyl acetate was stirred vigorously for 10 minutes at room temperature and treated with a solution of n-butylisocyanate (1.0 g, 10 mM) in ethyl acetate (10 ml). The mixture was stirred for 2 hours, filtered and the organic layer separated, washed with water (20 ml), dried (MgSO$_4$) and evaporated. There was thus obtained 5-n-butyl-S-methylisothiobiuret (1.7 g, 45% yield) as an oil; NMR (CDCl$_3$): 0.89–0.98(3H, t,$CH_3$), 1.22–1.58(4H, complex, $CH_2$—$CH_2$), 2.37(3H,s,S$CH_3$), 3.15–3.25(2H,q,N$CH_2$), 4.7–7.2(3H, broad, NH$_2$, NH).

(ii) A mixture of 5-n-butyl-S-methylisothiobiuret (9.45 g, 50 mM) and triethyl orthoacetate (20 ml, 118 mM) was heated at reflux for 5 hours. Excess triethyl orthoacetate was removed by distillation and the residue was distilled at 0.2 mm Hg. The fraction which distilled at 160° C. was collected to give 1-n-butyl-2-methyl-4-methylthio-1,3,5-triazin-6-one (7.2 g, 68% yield) as a solid, mp 62°–63° C.; microanalysis, found: C, 51.0; H, 7.1; N, 20.0%; $C_9H_{15}N_3OS$ requires: C,50.7; H, 7.0; N, 19.7%; NMR: 1.0 (3H,t,$CH_3$), 1.3–1.5(2H,m,$CH_2$), 1.62–1.82(2H,m,$CH_2$), 2.5(6H,s,C$CH_3$ and S$CH_3$), 3.9–4.0(2H, t,N$CH_2$).

(iii) A mixture of 1-n-butyl-2-methyl-4-methylthio-1,3,5-triazin-6-one (0.213 g 1 mM) and N-ethylaniline was heated at 190°–195° C. under an atmosphere of argon for 16 hours. The cooled solution was subjected to flash column chromatography. Elution with EtOAc/hexane (1/3) removed ethylaniline and elution with EtOAc/hexane (1/1) gave the anilino triazinone as a gum which was dissolved in ethyl acetate and treated with excess ethereal hydrogen chloride. The mixture was evaporated to dryness and the residue recrystallised from a mixture of acetone and diethyl ether to give 1-n-butyl-4-N-ethylanilino-2-methyl-1,3,5-triazin-6-one hydrochloride as a solid (0.154 g., 48% yield), mp 127°–129° C.; microanalysis, found:C, 60.3; H, 6.8; N, 17.1% $C_{16}H_{23}N_4OCl$ requires: C, 59.5; H, 7.1; N, 17.4%; NMR: 0.9(3H,t,$CH_3$), 1.1(3H,t,$CH_3$), 1.22–1.40(2H,m,$CH_2$), 1.5–1.65(2H,m,$CH_2$), 2.3–2.5(3H, broad, $CH_3$), 3.75–3.85(2H,t,N$CH_2$), 3.85–4.0 (2H, hidden by $H_2O$, $CH_2$), 7.2–7.5(5H, complex, aromatic).

The free base was obtained by partitioning the hydrochloride salt between saturated aqueous sodium carbonate and methylene chloride. The layers were separated, the organic layer dried and the solvent evaporated to give the free base.

EXAMPLE 36

A mixture of 1-n-butyl-4-N-ethylanilino-2-methyl-1,3,5-triazin-6-one (1.0 g, 3.1 mM) and phosphorus oxychloride (20 ml) was heated at reflux for 5 hours. Excess phosphorus oxychloride was evaporated in vacuo and the residue azeotroped with toluene (2×10 ml). The residue was cooled to 5° C. and treated with methylamine in IMS (33% w/w, 20 ml), kept at room temperature for eighteen hours, heated at reflux for 30 minutes and then evaporated to dryness. The residue was dissolved in hydrochloric acid (2M, 20 ml), extracted with ether and the ether layer discarded. The aqueous solution was extracted with methylene chloride (4×10 ml) and the combined extracts dried (MgSO$_4$) and evaporated. The residue was purified by flash column chromatography using 10% methanol in methylene chloride as eluant to give 6-n-butylamino-1,2-dimethyl-4-N-ethylanilino-1,3,5-triazinium chloride demihemihydrate as a solid, mp 171°–174° C.; microanalysis, found: C,59.9; H, 8.0; N, 20.5%; $C_{17}H_{26}N_5Cl$. 0.25 $H_2O$ requires: C, 60.0; H, 7.8; N, 20.6%; NMR: 0.7 and 1.0(2×3H, t, C$CH_3$ rotamers), 1.2–1.8(2×2H, m, $CH_2$ rotamers), 1.25 (3H,t,$CH_3$), 2.35 and 2.65 (2×3H, s, $CH_3$ rotamers), 3.5(3H,?, N$CH_3$), 3.0 and 3.55 (2×2H,q,$CH_2$ rotamers), 4.05 (2H,m,N$CH_2$), 7.2–7.53(5H, complex, aromatic), 8.8 and 9.0 (2×1H, br, NH rotamers).

The quaternary group was confirmed as methyl by nuclear Overhauser studies.

EXAMPLE 37

A mixture of 2-methyl-6-methylamino-4-(3-methyl-piperidino)-1,3,5-triazine (221 mg; 1 mM) and methyl iodide (0.5 ml; 8 mM) and dioxane (5 ml) was heated at reflux for 15 hours. The mixture was cooled, the solvent removed under reduced pressure and the residue was crystallised from a mixture of methanol and ether. There was thus obtained 1,2-dimethyl-6-methylamino-4-(3-methylpiperidino)-1,3,5-triazinium iodide (262 mg, 72% yield) m.p. 214°–214.5° C.; microanalysis found: C,39.7; H,5.8; N,19.3%; $C_{12}H_{22}N_5I$ requires: C,39.7; H,6.1; N,19.3%; NMR (200 MHz). ($CDCl_3$): 0.95–1.05 (3H,q, piperidine 3—$CH_3$), 1.2–2.0 (5H, complex, piperdine 3H, 4—$CH_2$ and 5—$CH_2$), 2.5–2.6 (3H, s, $CH_3$), 2.6–3.15 (2H, complex, piperidine 2—H axial and 6—H axial), 3.05–3.15 (3H,d, $NHCH_3$), 3.9 (3H,s, N—$CH_3$), 4.45–4.7 (2H, complex piperidine 2—H equatorial and 6—H equatorial), 8.6–8.8 (1H, br, NH). [Note: the site of quaternisation was confirmed by conventional nuclear Overhauser studies].

The triazine starting material was prepared as follows:

A mixture of 4-chloro-2-methyl-6-methylamino-1,3,5-triazine (1.06 g; 6.7 mM; described in J. Pharm. Soc. (Japan) 1975, 95, p.512) and 3-methylpiperidine (1.32 g, 13.3 mM) in acetone (10 ml) was stirred at ambient temperature for 6 hours. The mixture was filtered and the solid was partitioned between 3N aqueous ammonia solution (50 ml) and dichloromethane (50 ml). The organic solution was separated and dried ($MgSO_4$) and the solvent was removed, and the residue was crystallised from elthanol. There was thus obtained 2-methyl-6-methylamino-4-(3-methylpiperidino)-1,3,5-triazine (608 mg, 41.3% yield) m.p. 155°–155.50° C.; microanalysis found: C,59.9; H,8.7; N,31.6%; $C_{11}H_{19}N_5$ requires C,59.7; H,8.6; N,31.7%.

The site of quaternisation was confirmed by conventional nuclear Overhauser studies.

EXAMPLE 38–49

The procedure described in Example 37 was repeated using the appropriate substituted amino-1,3,5-triazine of the formula VI and methyl iodide. The following compounds of formula I ($R^1=R^2$=methyl; $Y^-$=iodide) were thus obtained:

| Ex | P | $R^6$ | m.p. (°C.) | Recyst Solvent(s) | Yield (%) |
|---|---|---|---|---|---|
| 38 | Me, Me-piperidino | methylamino | 226–226.5 | MeOH/ether | 72 |
| 39 | Me-piperidino | ethylamino | 150–150.5 | EtOAc | 46 |
| 40 | $PhCH_2$-piperidino | methylamino | 207–208 | EtOH/ether | 71 |
| 41 | Ph-piperidino | methylamino | 232.5–233 | EtOH/ether | 73 |
| 42 | Ph-pyrrolidino | methylamino | 225–227 | MeOH/EtOAc | 31 |
| 43 | Me-pyrrolidino | methylamino | 201–202 | MeOH/EtOAc | 40 |
| 44 | Et-piperidino | methylamino | 157–159.5 | EtOAc | 62 |

-continued

| Ex | P | R⁶ | m.p. (°C.) | Recyst Solvent(s) | Yield (%) |
|----|---|-----|-----------|-------------------|-----------|
| 45 | Me / Me cis (piperidinyl) | methylamino | 217–218.5 | MeOH/EtOAc | 77 |
| 46 | nC₃H₇ (piperidinyl) | methylamino | 173–176 | EtOAc/n-hexane | 49 |
| 47 | PhCH₂ (piperidinyl) | methylamino | 183.5–185 | MeOH/EtOAc | 15 |
| 48 | Et (piperidinyl) | methylamino | 175–176.5 | MeOH/EtOAc | 62 |
| 49 | nC₄H₉ (piperidinyl) | methylamino | 146–148 | EtOAc | 39 |

The necessary starting materials of formula VI (R² = methyl) were obtained as solids in an analogous manner to that for Example 1 by reaction of the appropriate 4-chloro-1,3,5-triazine of formula VII (X = chloro) with the appropriate amine of formula VIV, and had the following properties:

| No | P | R⁶ | m.p. (°C.) | Recyst Solvent(s) | Yield (%) |
|----|---|-----|-----------|-------------------|-----------|
| 2 | Me, Me (piperidinyl) | methylamino | 136–137.5 | toluene/n-hexane | 17 |
| 3 | Me (piperidinyl) | ethylamino | 77–78 | n-hexane | 54 |
| 4 | PhCH₂ (piperidinyl) | methylamino | 144–145 | aq.MeOH | 58 |
| 5 | Ph (piperidinyl) | methylamino | 203–204 | iPrOH | 58 |
| 6 | Ph (pyrrolidinyl) | methylamino | 151–153 | EtOAc | 61 |

-continued

| No | P | R⁶ | m.p. (°C.) | Recyst Solvent(s) | Yield (%) |
|----|---|----|-----------|-------------------|-----------|
| 7  | Me-piperidin-4-yl (N-linked) | methylamino | 121–122 | EtOAc | 59 |
| 8  | 4-Et-piperidin-1-yl | methylamino | 115–116 | n-hexane | 36 |
| 9  | cis-3,5-diMe-piperidin-1-yl | methylamino | 176–178 | EtOH | 68 |
| 10 | 4-nC₃H₇-piperidin-1-yl | methylamino | 97–98.5 | n-hexane | 80 |
| 11 | 4-PhCH₂-piperidin-1-yl | methylamino | 119–120 | n-hexane | 39 |
| 12 | 2-Et-piperidin-1-yl | methylamino | 114–116 | EtOAC | 43 |
| 13 | 4-nC₄H₉-piperidin-1-yl | methylamino | 83.5–84.5 | n-hexane | 65 |

Note: The starting material used to prepare the intermediate 3, that is 4-chloro-6-ethylamino-2-methyl-1,3,5-triazine was prepared as described by T. Tsujikawa et alia in *J. Pharm Soc* (Japan), 1975, 95, 572.

EXAMPLE 50

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (b) Capsule | mg/capsule |
| Compound X | 10 |
| Lactose Ph. Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

Scheme I

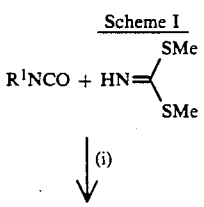

-continued
Scheme I
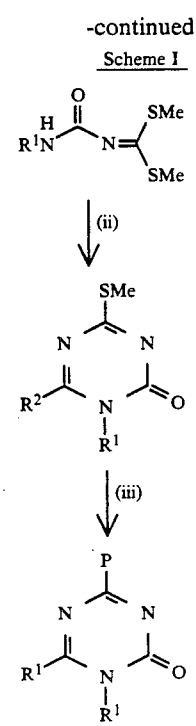
Typical conditions/reagents:
(i) Room Temperature, Na$_2$CO$_3$
(ii) R$^2$C(OEt)$_3$, heat
(iii) amine of formula (II) or formula (III), heat
-continued
Scheme I
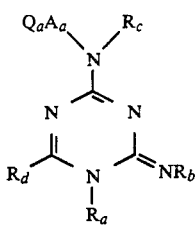 (XIa)
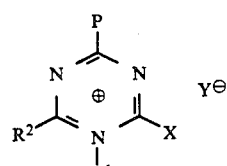 (XII)
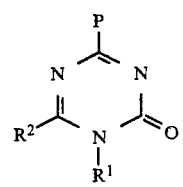 (XIII)
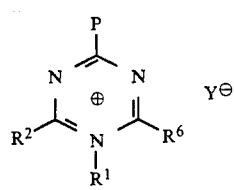 (I)
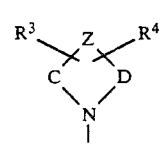 (II)
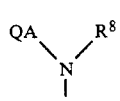 (III)
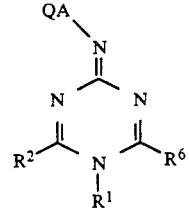 (IVa)
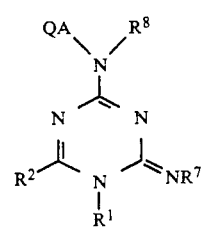 (IVb)

29

-continued
Scheme I

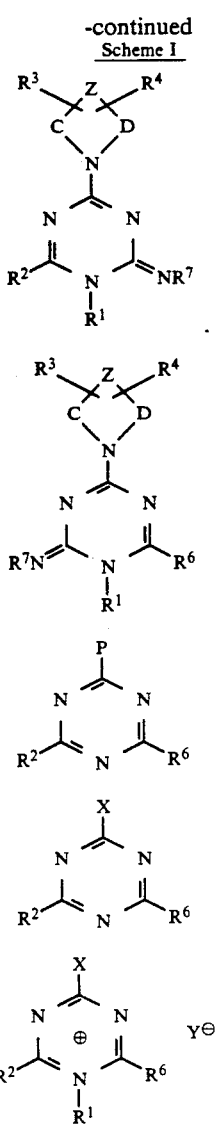

We claim:
1. A compound of the formula I

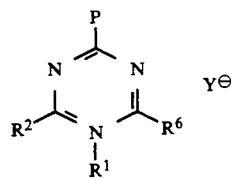

wherein:
P is a group of formula

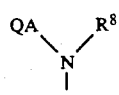

III $R^1$ is (1-10C)alkyl, (3-8C)cycloalkyl, (3-8C)cycloalkyl-(1-4C)alkyl, phenyl or phenyl(1-4C)alkyl;
$R^2$ is hydrogen, (1-4C)alkyl, amino or (1-4C)alkylamino;
$R^6$ is (1-4C)alkyl, amino or (1-6C) alkylamino;

30

$R^8$ is hydrogen, (3-6C)cycloalkyl-(1-4C)alkyl, (1-6-C)alkyl, (3-6C)alkenyl, (3-6C)alkynyl or phenyl(-1-4C)alkyl; or $R^8$ is a (1-4C)alkylene or (2-4C-)alkenylene linked to the nitrogen atom of the group Q.A.N—, either of which linking groups may optionally bear a (1-4C)alkyl, phenyl or phenyl(1-4C)alkyl substituent and either of which linking groups thereby completes a ring including two adjacent carbon atoms of ring Q, any carbon atoms in A and the adjacent nitrogen atom of the group —A.N—;
A is a direct bond to the group —N($R^8$)— or is (1-6C)alkylene;
Q is a phenyl or pyridyl moiety;
Y is a physiologically acceptable anion;
and wherein any one or more of said phenyl, benzene or pyridyl moieties in $R^1$, $R^8$ and Q may optionally be unsubstituted or bear one or more substituents independently selected from halogeno, (1-4C)alkyl, (3-6C)alkenyl, (1-4C)alkoxy, cyano, trifluoromethyl, nitro, amino, hydroxy, (1-4C)alkylamino, dialkylamino of up to six carbon atoms, (1-4C)alkylthio, (1-4C)alkylsulphinyl, (1-4C)alkylsulphonyl and (1-4C)alkylenedioxy;
but excluding compounds in which Q is phenyl, A is a direct bond, $R^1$ is phenyl, $R^8$ is hydrogen, $R^2$ and $R^6$ are both amino, and Y is a physiologically acceptable anion.
2. A compound of formula XI

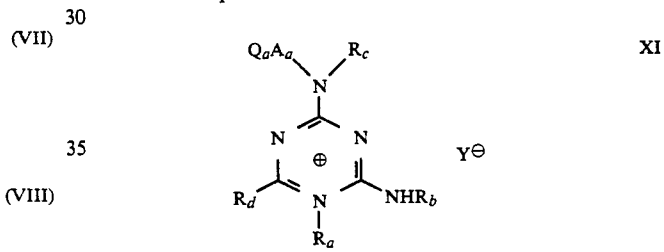

XI wherein: Ra is (1-4C)alkyl; Rb is (1-4C)alkyl; Rc is (1-6C)alkyl, (3-6C)alkenyl, (3-6C)alkynyl or phenyl(-1-4C)alkyl; or Rc is (1-4C)alkylene or (2-4C)alkenylene linked to the nitrogen atom of the group Qa-.Aa.N—, either of which linking groups may optionally bear a (1-4C)alkyl substituent and either of which linking groups thereby completes a ring including two adjacent carbon atoms of Q and the nitrogen of group —Aa.N—; Rd is (1-4C)alkyl; Qa is phenyl; Aa is a direct bond to the group —NRc—; and Y is a physiologically acceptable anion.
3. A compound as claimed in any one of the preceding claims in which Y is selected from halide, sulphate, fluoroborate, phosphate, nitrate, acetate, benzoate, butyrate, citrate, tartrate, dibenzoyltartrate, fumarate, trifluoroacetate, methosulphate, and p-toluenesulphonate.
4. A compound selected from formulae IVa, IVb, or a tautomeric form thereof

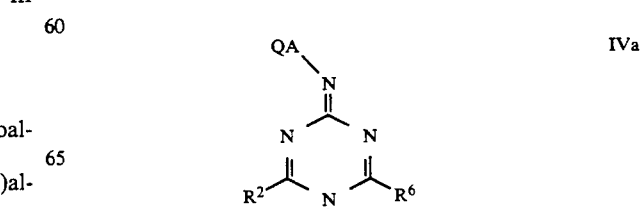

IVa

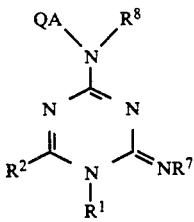

IVb wherein
R¹ is (1-10C)alkyl, (3-8C)cycloalkyl, (3-8C)cycloalkyl-(1-4C)alkyl, phenyl or phenyl(1-4C)alkyl;
R² is hydrogen, (1-4C)alkyl, amino or (1-4C)alkylamino;
R⁶ is (1-4C) alkyl, amino or (1-6C) alkylamino;
R⁸ is hydrogen, (3-6C)cycloalkyl-(1-4C)alkyl, (1-6C)alkyl, (3-6C)alkenyl, (3-6C)alkynyl or phenyl(1-4C)alkyl; or R⁸ is a (1-4C)alkylene or (2-4C)alkenylene linked to the nitrogen atom of the group Q.A.N—, either of which linking groups may optionally bear a (1-4C)alkyl, phenyl or phenyl(1-4C)alkyl substituent and either of which linking groups thereby completes a ring including two adjacent carbon atoms of ring Q, any carbon atoms in A and the adjacent nitrogen atom of the group —A.N—;
A is a direct bond to the group —N(R⁸)— or is (1-6C)alkylene;
Q is a phenyl or pyridyl moiety;
and R⁷ is hydrogen or (1-4C)alkyl; provided that when Q is phenyl, A is a direct bond and R¹ is phenyl, then R² and R⁶ are not both amino.

5. A compound selected from formula Xa or XIa (or a tautomeric form thereof)

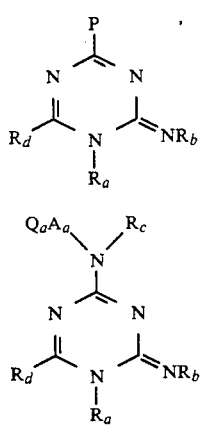

wherein
P is a group of formula

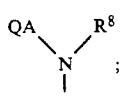

R⁸ is hydrogen, (3-6C)cycloalkyl-(1-4C)alkyl, (1-6C)alkyl, (3-6C)alkenyl, (3-6C)alkynyl or phenyl(1-4C)alkyl; or R⁸ is a (1-4C)alkylene or (2-4C)alkenylene linked to the nitrogen atom of the group Q.A.N—, either of which linking groups may optionally bear a (1-4C)alkyl, phenyl or phenyl(1-4C)alkyl substituent and either of which linking groups thereby completes a ring including two adjacent carbon atoms of ring Q, any carbon atoms in A and the adjacent nitrogen atom of the group —A.N—;
A is a direct bond to the group —N(R⁸)— or is (1-6C)alkylene;
Q is a phenyl or pyridyl moiety;
Ra is (1-4C)alkyl; Rb is (1-4C)alkyl; Rc is (1-6C)alkyl, (3-6C)alkenyl, (3-6C)alkynyl or phenyl(1-4C)alkyl; or Rc is (1-4C)alkylene or (2-4C)alkenylene linked to the nitrogen atom of the group Qa-.Aa.N—, either of which linking groups may optionally bear a (1-4C)alkyl substituent and either of which linking groups thereby completes a ring including two adjacent carbon atoms of Q and the nitrogen of group —Aa.N—; Rd is (1-4C)alkyl; Qa is phenyl; Aa is a direct bond to the group —NRc—.

6. A pharmaceutical composition comprising an active ingredient selected from a compound of formula I as claimed in claim 1, a compound of formula XI as claimed in claim 2, or an ahydro-base as claimed in claim 4 or 5, together with or in admixture with a pharmaceutically-acceptable diluent or carrier.

7. A method of modulating the action of the sinoatrial node in a warm-blooded animal requiring such treatment which comprises administering to said animal an effective amount of a pharmacologically active agent selected from the group consisting of a compound of the formula I as claimed in claim 1, a non-ionic form thereof having the formula IVa, IVb, (or a tautomeric form thereof) as claimed in claim 4, or a non-ionic form of said formula I compound having the formula Xa or XIa as claimed in claim 5.

8. A compound as claimed in claim 1 wherein R¹ is methyl, ethyl, propyl, butyl, cyclopentyl, cyclohexyl, cycloheptyl cyclopropylmethyl, cylopentylmethyl, cyclohexylmethyl, 2-(cyclohexyl)ethyl, benzyl, 1-phenylethyl or 2-phenylethyl; R2 is hydrogen, methyl or ethyl; R⁶ is amino, methylamino, ethylamino, propylamino, butylamino, methyl or ethyl; and P is a group of formula III in which R⁸ is methyl, ethyl, propyl, isopropyl, butyl, iso-butyl sec-butyl, allyl, but-2-enyl, 2-methyl-2-propenyl, prop-2-ynyl, but-2-ynyl, cyclopropylmethyl, cylopentylmethyl, cyclohexylmethyl, 2-(cyclohexyl)ethyl, benzyl, 1-phenylethyl or 2-phenylethyl; or R⁸ is linked to the nitrogen atom of the group QAN by a methylene, ethylidene, ethylene, isopropylidene, trimethylene, tetramethylene, vinylene or 1,3-propenylene linking group, any of which linking groups may bear a methyl, ethyl, propyl, butyl, phenyl, benzyl, 1-phenylethyl or 2-phenylethyl substituent; Q is phenyl or pyridyl; A is a direct bond, methylene, ethylene, trimethylene or tetramethylene, any of which may optionally bear one or two methyl substituents; and wherein one or more of the phenyl or benzene moiety in R1, Q or R8 is optionally substituted by fluoro, chloro, bromo, methyl, ethyl, allyl, methoxy, ethoxy, methylamino, ethylamino, dimethylamino, diethylamino, methylthio ethylthio, methylsulphinyl, ethylsulphinyl, methylsulphonyl, ethylsulphonyl, methylenedioxy, and isopropylidenedioxy.

9. A compound as claimed in claim 1 wherein P is a group of formula III in which Q is phenyl, 4-chlorophenyl, 4-methylphenyl, 2-nitrophenyl, 2-methoxyphenyl, 4-methylthiophenyl, 2,5-dinitrophenyl, 3,5-dimethylphenyl, or 3,5-dichlorophenyl; A is a direct bond; and $R^8$ is methyl, ethyl, propyl, isopropyl, butyl, iso-butyl sec-butyl, allyl, but-2-enyl, 2-methyl-2-propenyl, prop-2-ynyl, but-2-ynyl, cyclopropylmethyl, cylopentylmethyl, cyclohexylmethyl, 2-(cyclohexyl)ethyl, benzyl, 1-phenylethyl or 2-phenylethyl; or P is a group of formula III which comprises 1-indolinyl, 1-indolyl, 3-methyl-1-indolinyl, 3-methyl-1-indolyl, 3-ethyl-1-indolyl, 3-ethyl-1-indolinyl, 5-bromo-1-indolyl, 1,2,3,4-tetrahydro-1-quinolyl, 1,2,3,4-tetrahydro-2-isoquinolyl, 5-aza-1-indolinyl, 3-propyl-1-indolyl or 3-propyl-1-indolinyl, 2-methyl-1-indolyl and 2-methyl-1-indolinyl.

10. A compound as claimed in claim 1 wherein the triazinium cation is selected from 1,2-dimethyl-4-N-ethylanilino-6-methylamino-1,3,5-triazinium;
1,2-dimethyl-4-(3-ethylindol-1-yl)-6-methylamino-1,3,5-triazinium;
1,2-dimethyl-4-N-allylanilino-6-methylamino-1,3,5-triazinium;
1,2-dimethyl-4-N-(2-butynyl)anilino-6-methylamino-1,3,5-triazinium;
1,2-dimethyl-4-N-cyclopropylmethylanilino-6-methylamino-1,3,5-triazinium; and
1,2-dimethyl-4-N-ethylanilino-6-ethylamino-1,3,5-triazinium; and Y is a physiologically-acceptable counter-anion.

* * * * *

UNITED STATES PATENT AND TRADEMARK OFFICE
CERTIFICATE OF CORRECTION

PATENT NO. : 5,332,737
DATED : July 26, 1994
INVENTOR(S) : Mills et al

It is certified that error appears in the above-indentified patent and that said Letters Patent is hereby corrected as shown below:

Column 29, line 50, claim 1, formula I should read as follows (showing a positive charge in the triazine ring and the formula designation (I)):

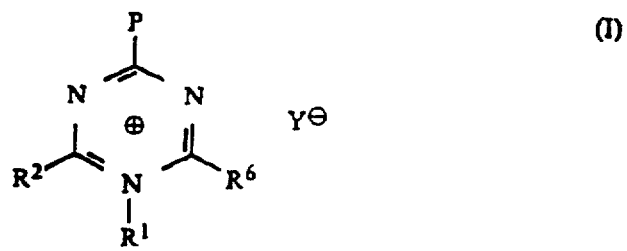

(I)

Signed and Sealed this

Fifth Day of March, 1996

Attest:

BRUCE LEHMAN

Attesting Officer

Commissioner of Patents and Trademarks